(12) United States Patent
Winkler (10) Patent No.: US 6,491,035 B2
(45) Date of Patent: Dec. 10, 2002

(54) GLANCE SHEATH PROPHYLACTIC WITH INVERTED, COMPACTED RESERVOIR AND METHOD OF MANUFACTURING SUCH A DEVICE

(76) Inventor: John Andrew Winkler, 600 N. Pantano Rd. #121, Tucson, AZ (US) 85710

( * ) Notice: Subject to any disclaimer, the term of this patent is extended or adjusted under 35 U.S.C. 154(b) by 0 days.

(21) Appl. No.: 09/752,864

(22) Filed: Dec. 30, 2000

(65) Prior Publication Data

US 2002/0083950 A1 Jul. 4, 2002

(51) Int. Cl.[7] ................................................ A61F 6/02
(52) U.S. Cl. ........................ 128/842; 128/844; 128/918
(58) Field of Search ................................. 128/842, 844, 128/918; 604/347–353

(56) References Cited

U.S. PATENT DOCUMENTS

| | | | |
|---|---|---|---|
| 3,648,700 A | 3/1972 | Warner | |
| 3,677,225 A | 7/1972 | Czirely | |
| 4,320,752 A | 3/1982 | Comparetto | |
| 4,821,742 A | * 4/1989 | Phelps | 128/842 |
| 4,869,269 A | 9/1989 | Sharkan | |
| 5,102,405 A | 4/1992 | Conway | |
| 5,421,350 A | 6/1995 | Friedman | |
| 5,458,114 A | 10/1995 | Herr | |
| 5,477,865 A | 12/1995 | Broad, Jr. | |
| 5,531,725 A | * 7/1996 | Steer | 604/349 |
| 6,098,625 A | 8/2000 | Winkler | |

* cited by examiner

Primary Examiner—Michael A. Brown

(57) ABSTRACT

A glans sheath device having a reservoir capable of containing preferrably 8 cc's of seminal fluid and having said reservoir compacted and packaged to be protected and remain compacted during coitus and able to deploy distally outward to contain seminal fluid flooding the reservoir. Restraining legs attached to the perimeter of the glans sheath flange tautly restrain the flange over a multiple-piece restraining tool so that the glans sheath can be easily handled during a flange to glans bonding operation. A protective backing covers over adhesive on the proximal surface of the flange to protect the adhesive prior to bonding.

21 Claims, 13 Drawing Sheets

GLANCE SHEATH PROPHYLACTIC WITH INVERTED, COMPACTED RESERVOIR AND METHOD OF MANUFACTURING SUCH A DEVICE

FIELD OF THE INVENTION

This invention relates to the field of prophylactics known as micro-condoms, penile caps or glans sheaths as defined by the United States Food and Drug Administration.

Prophylactic devices which attach only to the glans penis are identified by the United States Food and Drug Administration as glans sheaths. These devices attach either by adhesive means or by restraining means such as a constricting grip. For those devices which adhere to the penis only about the tip, the reservoir volume of the sheath must be large enough in size to contain the quantity of ejaculate discharged into the reservoir. Roll-down condom prophylactics do not have this reservoir volume issue as the ejaculate discharge can fill into the full volume of the roll-down condom. A glans sheath reservoir which is unable to accomodate the produced volume of ejaculate becomes pressurized by the strong contractions of the muscles producing the ejaculation. This fluid pressure can easily compromise the bondline of the adhesive securing the glans sheath to the glans penis.

The instant invention is a glans sheath designed to have a reservoir volume capable of containing approximately 8 cc's of fluid. The reservoir is packaged such that the reservoir is not distally positioned relative to the bonding flange once packaged, but is inverted proximally and folded over upon itself. Inverting and folding the reservoir evacuates air from the reservoir and protects the reservoir prior to its deployment.

BACKGROUND OF THE INVENTION

Glans sheath prophylactics such as U.S. Pat. Nos. 3,677,225, 3,648,700, 4,320,752, 4,821,742, 4,869,269, 5,102,405, and 5,421,350 all have a fundamental flaw as a glans sheath. All of these devices provide no method of evacuating air from the resevoir volume during the manufacturing operation. Additionally, these devices do not take measures to ensure that the evacuated air remains removed prior to glans bonding. Without this critical step of evacuating the reservoir air prior to bonding, all of the ejaculate discharge entering into the reservoir volume competes with trapped air for space and this pressurizes the reservoir above ambient atmospheric pressure. This overpressure is great enough to cause localized failure of the bonded area of the flange of the glans sheath. This localized failure is identified as a small fissure separation of the adhered flange from the glans. Seminal discharge erupts through this small fissure, completely defeating the contraceptive intention of the device. Reservoir air evacuation is not an exercise that should be left to the user bonding the device to the glans. Evacuation should be included as a manufacturing step. The instant invention incorporates reservoir evacuation and reservoir packaging into the manufacturing process.

U.S. Pat. No. 5,458,114 addresses both design issues of forming a reservoir large enough to contain a typical seminal discharge volume and packaging this reservoir volume to ensure that air evacuated from the reservoir volume remains evacuated prior to bonding. This design has other flaws.

In U.S. Pat. No. 5,458,114 the protective retaining structure packaging the reservoir of the device must be mechanically affixed to the distal surface of the sheath flange. This manufacturing step lowers the reliability of the device in that the retaining structure must be mechanically attached to the bowl structure. Should the retaining structure physically separate from the bowl during coitus, it would have to be retrieved by a medical professional if it were to become lodged in a body cavity. Further, the retaining structure is designed to have a star shaped pattern which the bladder must be forced through as the bladder deploys. Depending on the rigidity of the retaining structure, this material will oppose the bladder attempting to deploy itself and the weaker path of resistance for the pressurized ejaculate becomes the bondline of the bowl adhered to the skin of the glans. Should the bondline fail by the creation of a fissure as described, the contraceptive intention of the patented device is defeated.

U.S. Pat. No. 5,477,865 is a roll-down prophylactic which also inverts the reservoir during its manufacture. The fundamental flaw with this design is that the inverted reservoir cannot be rolled up or folded onto itself once inverted. This leaves the design with two options. The design can have a small enough reservoir that it is not necessary to roll or fold the reservoir to avoid damage to the reservoir during coitus. In this case, the reservoir will likely re-invert itself back to its original distal position once the user tries to apply the condom simply from air pressure inside the condom. A condom with a small reservoir as described does not offer much ejaculate containment volume and is essentially a commercially available condom with the small reservoir tip turned inside out. Ideally an inverted reservoir would be large enough to contain greater than 5 cc's of fluid. A reservoir this large should be folded or somehow packaged to remain at the tip of the glans near the urethral opening once inverted. Without some variation of a restraining mechanism, such as a flap, to keep the inverted reservoir folded up, the reservoir will spring back to its elongated shape and will face proximally. Once the reservoir is sprung and extended proximally, the user can only push the reservoir off to the side during roll down application. Pushed off to the side, the reservoir will extend down the interior length of the condom rolled down onto the penis and is then firmly wedged between the glans or shaft of the user's penis and the interior wall of the condom rolled onto the penis. Wedged in this fashion, the reservoir is completely useless as it cannot be deployed because it is constrictively trapped between the condom sidewall and the user's penis. This is also an unsatisfactory option.

The instant invention discloses a glans sheath device which has a large reservoir volume to avoid overpressurization and the device is packaged so as to evacuate, fold and protect the reservoir without the addition of any external retaining structures to compromise reliability. During manufacturing the reservoir is inverted from its deployed distal position relative to the bonding flange of the glans sheath and instead lies in a compacted state facing the proximal direction of the device. In this orientation the reservoir is evacuated, folded and secured in place. By properly evacuating and folding the large reservoir during manufacturing of the instant invention, the reservoir is able to properly deploy when seminal discharge floods the reservoir yet the reservoir remains properly evacuated and constrained throughout coitus until reservoir flooding occurs.

Another issue which must be addressed is a method for handling a very pliable flange material. U.S. Pat. No. 6,098,625 by Winkler discloses a tool for tautly restraining the flange of that invention but does not utilize an efficient two-piece tool design as does the present invention. Winkler's invention must rely on proper separation between the tool and the flange after bonding the flange to the glans. There is also a likelihood that Winkler's design presents the opportunity for the flange to separate from the rigid tool before successful bonding which allows the creation of crevasses in the unbonded flange. The restraining legs of the instant invention differ in purpose from the force distribution strips of Winkler's design. Winkler intends the force distribution strips of U.S. Pat. No. 6,098,625 to remain affixed to the flange material to distribute tensile forces pulling the flange away from the glans penis during coitus.

SUMMARY OF THE INVENTION

The invented device is a glans sheath contraceptive which covers only the portion of the glans penis immediately surrounding the urethral opening. The device provides an adhesive coated annular flange as a means of attaching to the glans penis a collapsed, proximally oriented, folded reservoir capable of deploying when pressurized and able to contain ejaculate once deployed.

BRIEF DESCRIPTION OF THE DRAWINGS

FIGS. 5A through 7B illustrate alternative methods of applying an adhesive film to the proximal surface of an annular flange of a glans sheath.

DETAILED DESCRIPTION OF THE DRAWINGS

Figure 1A:
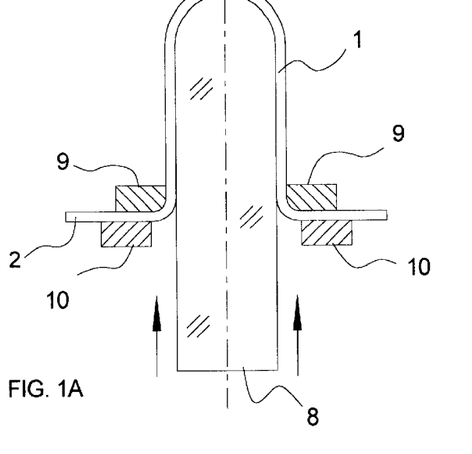
FIGS. 1A and 1B shows a cross-section of a deep draw operation being done to a sheet of plastic film to proximally extrude a reservoir volume from the sheet.
Figure 1B:
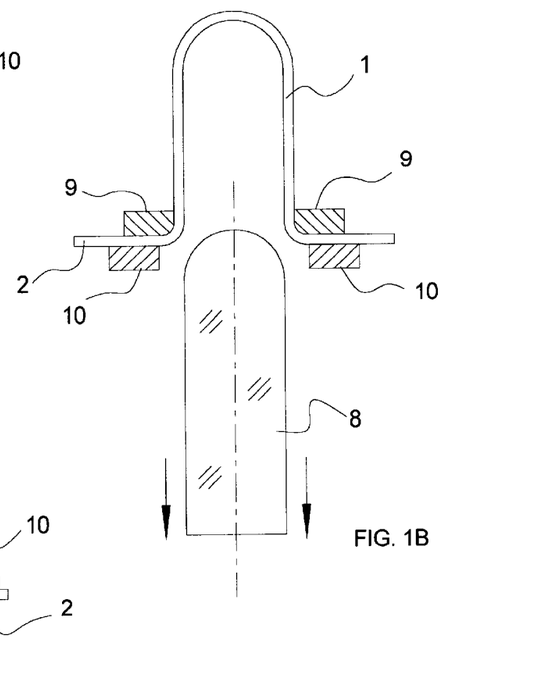
Figure 1C:
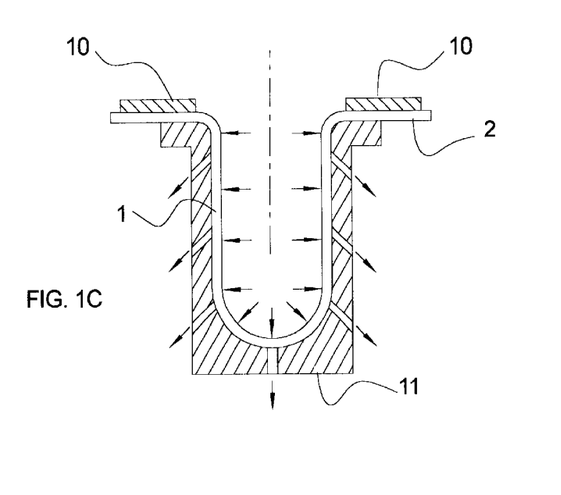
FIG. 1C shows a cross-section of a thermoform operation shaping a reservoir volume from a sheet of plastic film.

FIGS. 1A through 12B describe the invention and method of manufacturing in detail. Similar numbers denote similar items throughout the several figures. FIG. 1A shows a cross-section of a sheet of plastic film, such as a 0.8 mil thick polyethylene sheet known in the art, such as Stretchwrap polyethylene film, being deep drawn by an extrusion plunger 8 or any other forming means known in the art, to form a reservoir 1 for containing ejaculate from a user. During the extrusion process, the film is secured between an annular shaped, proximal manufacturing restraint 9 and an annular shaped distal manufacturing restraint 10, both made of a material known in the art such as plastic, rubber or metal. The restraints prevent creep of the film during the extrusion process. An annular-like flange 2 surrounding the reservoir 1 is formed from the film material and generally lies in a plane. As shown in FIG. 1B, after the film has been extruded the plunger 8 is withdrawn to leave the extruded reservoir volume 1 surrounded by the annular-like flange 2. An alternative method to forming the reservoir is shown in FIG. 1C. This method uses pressure differential between film proximal and distal surfaces to draw the film into a thermoforming vacuum chamber 11 to form the reservoir 1. This method can be done with or without the additional application of heat energy for better film flow into the forming cavity. During this forming process the generally planar, annular-like flange portion 2 is secured between the lip of the forming chamber 11 and a manufacturing restraint, such as a distal manufacturing restraint 10. The reservoir volume is extruded preferably towards the proximal surface of the surrounding annular flange but could be extruded distally and then inverted to be oriented proximally. Instead of performing an extrusion or thermoforming process, it is also possible to shape the reservoir and flange material using well-known elastomeric plastic dipping techniques avaible in the art such as latex dipping. A dipping method is not favorable due to the challenges of dipping a very thin film and maintaining even film thickness.

Figure 2A:
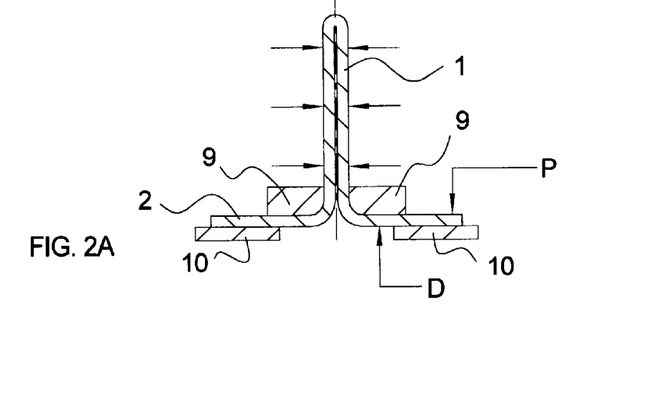
FIG. 2A shows a cross-section of a proximally extruded reservoir of a glans sheath being collapsed.

For the glans sheath device to be successful at containing ejaculate, it is critically important to evacuate the available air from the reservoir by collapsing the reservoir. Air within the reservoir volume occupies space that cannot be subsequently used to contain ejaculate from the user. The collapsing concept is shown in FIG. 2A where a general collapsing mechanism, denoted by the arrows, is forcing the available air out from the reservoir 1 as the reservoir projects above the proximal surface of the annular-like flange 2. The evacuation process is done while the device is held between a proximal manufacturing restraint 9 and a distal manufacturing restraint 10. The proximal and distal surfaces of the flange 2 are denoted with letters P and D, respectively.

Figure 2B:
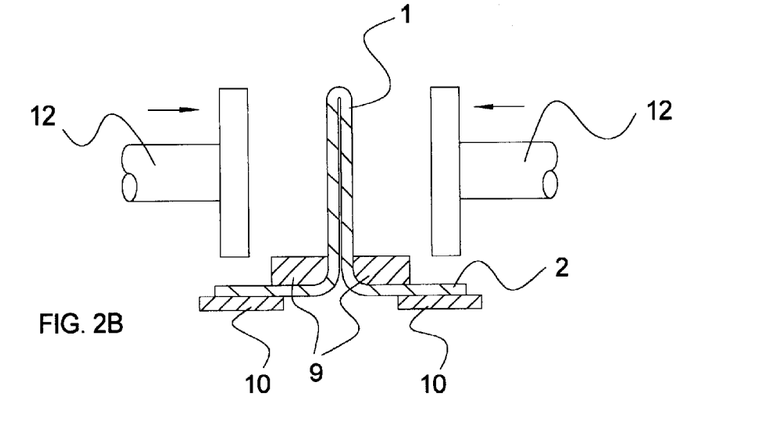
FIG. 2B shows a mechanical compression method of collapsing a reservoir volume of a glans sheath.
Figure 2C:
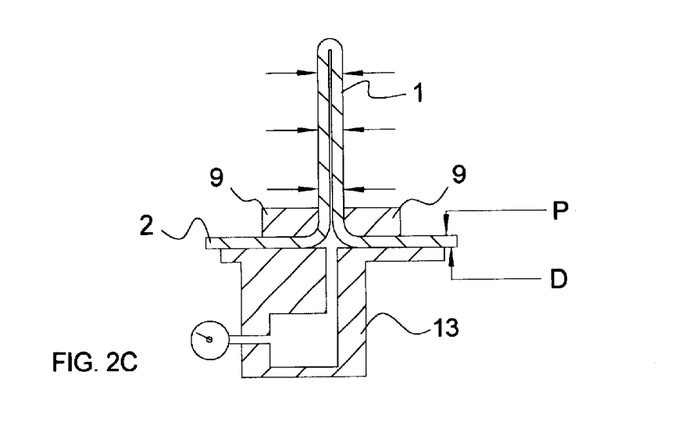
FIG. 2C shows a reservoir volume being collapsed by applying a vacuum to the interior of the reservoir of a glans sheath.

Several methods are available to collapse the reservoir to evacuate the volume. One method of mechanically collapsing the reservoir is shown in FIG. 2B. In FIG. 2B a mechanical deflation press 12 consisting of two or more opposing jaws advancing towards each other compresses the reservoir 1 to deflate the reservoir. Shown in FIG. 2C is another method of deflating the reservoir 1 by using a pressure differential. In this method the distal surface of the flange 2 is sealed against an evacuation chamber 13 by a proximal manufacturing restraint 9. A vacuum is drawn within the chamber to deflate and collapse the reservoir.

Figure 3A:
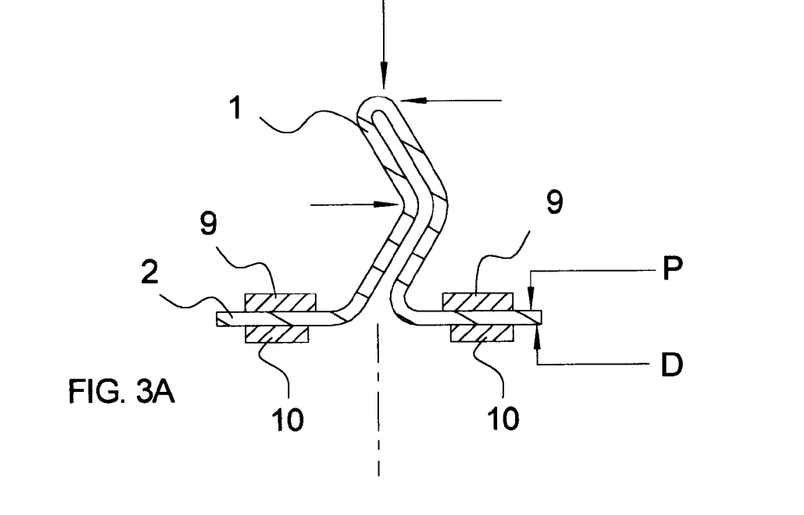
FIG. 3A shows a cross-section of an evacuated reservoir of a glans sheath being folded over so that it can be packaged.
Figure 3B:
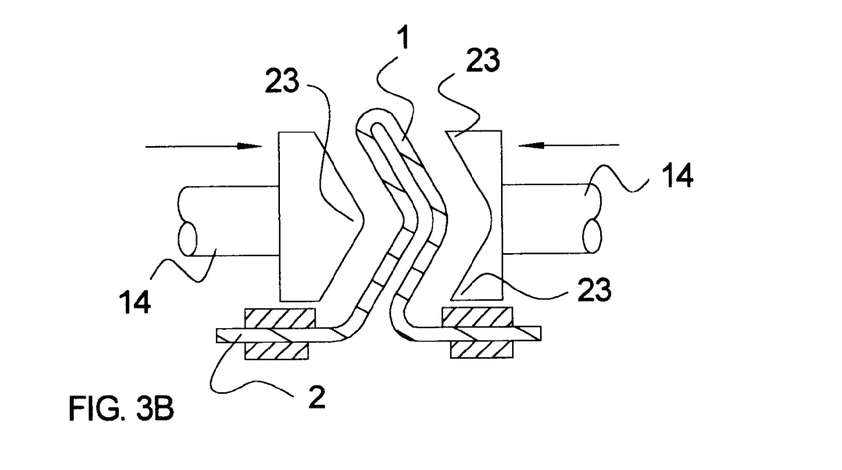
FIG. 3B demonstrates a mechanical folding operation acting to initiate a fold on a collapsed reservoir volume.

After being deflated the collapsed reservoir volume must be folded and packaged to protect the reservoir during coitus. FIG. 3A illustrates a general folding process for folding the reservoir 1 down onto the proximal surface of the restrained annular-like flange. Arrows show the direction and general location in which forces are applied to fold and compress the reservoir. FIG. 3B illustrates a mechanical method of folding the resevoir 1 using a mechanical reservoir folding initiation fixture 14 with blunt-tipped matching jaws opposing each other to initiate the fold in the reservoir. The blunt tips 23 of the jaws shown in the illustration total only three, two on one jaw, and one on the other, approximately equally spaced apart from each other. Any multiple number of blunt tips could be manufactured into the jaws to initiate more folds into the collapsed reservoir. Alternatively, any number of pins approximately equally spaced apart and approximately axially parallel to the flange proximal surface could be used as blunt edges mounted in a fashion to perform a crimping operation to initiate the folds in the reservoir. Alternatively, the reservoir could pass between rotating wheels with interlacing grooves to initiate folds. The operations of evacuating or deflating the reservoir and initiating folds in the reservoir could be achieved simultaneously instead of in multiple operations if the fold intiating mechanism 14 simply collapsed and thus evacuated the extruded reservoir during its compression operation.

Figure 3C:
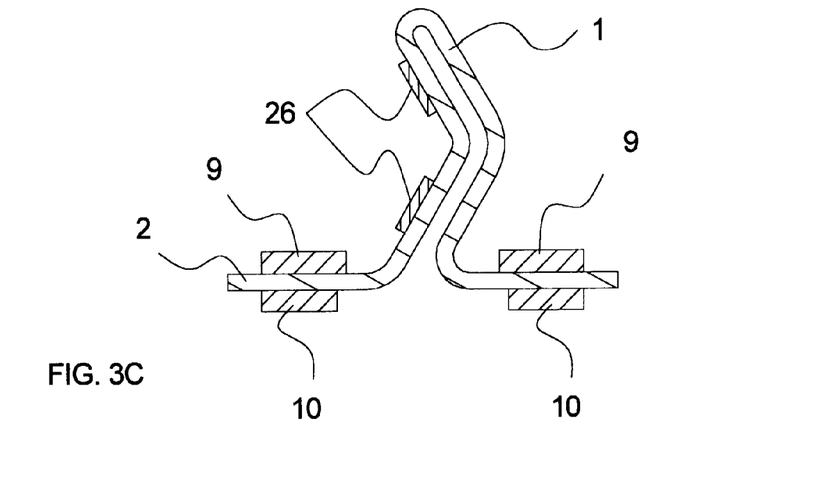
FIG. 3C demonstrates a low tack bonding agent being applied to the sidewall of an evacuated reservoir.

With the fold intitiated in the reservoir it is ready to be compacted into its final state. To ensure that it remains in this final state until it is deployed a low tack bonding agent is applied as shown in FIG. 3C. The water resistant low tack bonding agent 26 can be applied either as a film material such as 3M low tack double sided tape or applied as a spray such as diluted pine tar, which will adhere to the proximal surfaces of the reservoir 1 to help it remain in its compacted final state until deployment. It is important that the low tack bonding agent be water resistant so as to repel seminal pre-ejaculate which also fills into the reservoir. A water soluble bond agent would dissolve in the pre-ejaculate fluid and allow the reservoir to begin slowly deploying during coitus as the pre-ejaculate sloshes inside the reservoir.

Figure 3D:
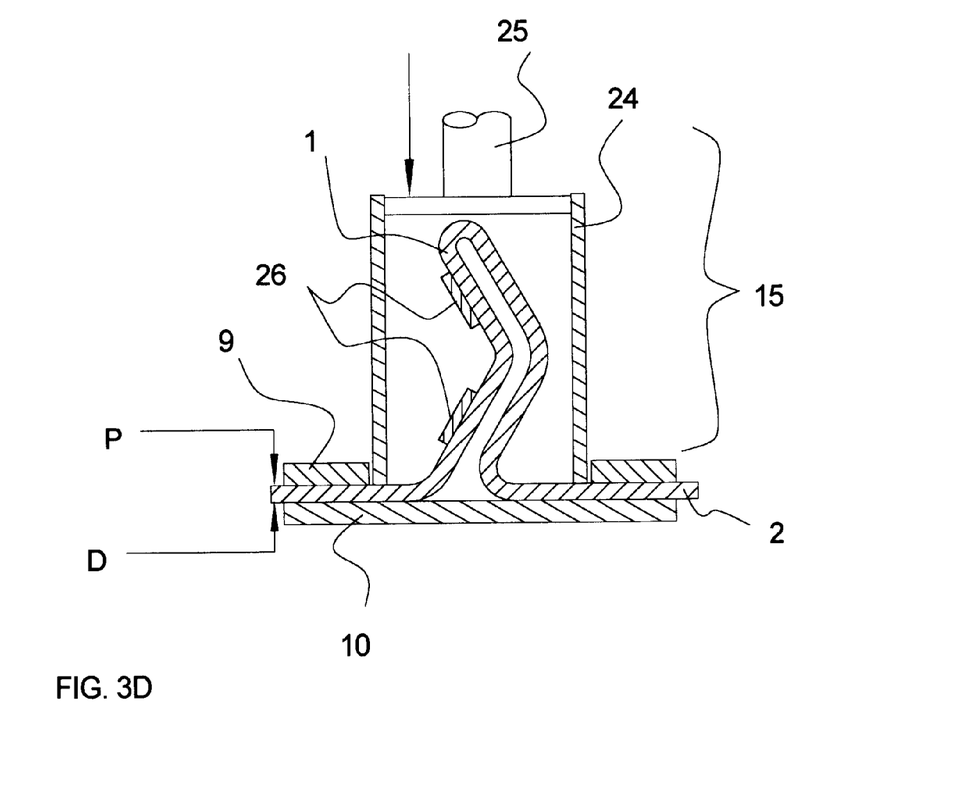
FIG. 3D demonstrates a mechanical press completing a folding operation by compressing and compacting an evacuated reservoir of a glans sheath.

Completion of the folding operation is shown in FIG. 3D. A mechanical reservoir folding completion fixture 15 is used to compact the reservoir 1 into its final state. The sidewall 24 of the fixture forms the envelope boundary in which the compacted reservoir will lie when a compacting piston or press 25 actuates to force the reservoir to fold down into its compacted state. Preferably this operation is done when the annular-like flange 2 is restrained by a proximal manufacturing restraint 9 of annular-like shape restraining the flange against a distal manufacturing restraint 10 of a generally planar shape. The generally planar restraint provides a surface which the compacting press can oppose to achieve maximum compression of the reservoir.

Figure 4A:
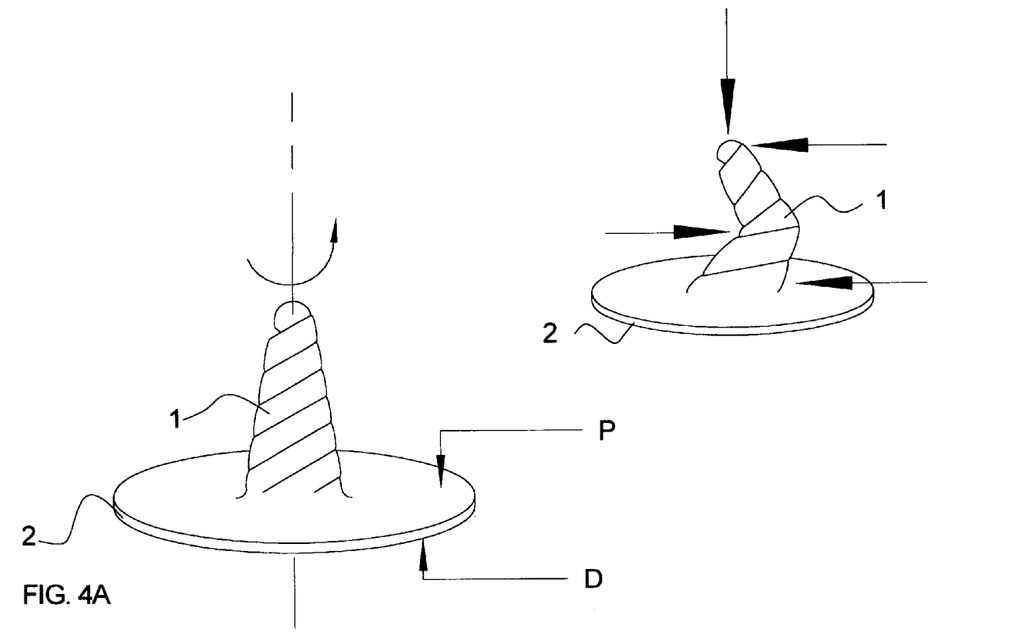
FIG. 4A shows an alternative method of removing the air from a reservoir volume by twisting the reservoir volume and then folding over the twisted reservoir of a glans sheath.

FIG. 4A shows an alternative method of evacuating the reservoir 1. The intention of this method is to force the available air from the reservoir by twisting the reservoir using a winding method to force the air from the reservoir. Proximal and distal manufacturing restraints as previously discussed would have to be used during a winding operation to restrain the annular-like flange. Restraints were not shown in the figure for reasons of clarity. After the winding method has forced the available air from the reservoir, similar fold intiating and reservoir compacting operations, shown by linear arrows in FIG. 4A, can be performed on the reservoir as previously discussed. Compacting would occur after a low tack bond agent has been applied to a portion of the proximal surface of the reservoir after fold initiation. Success of all evacuation and compaction methods relies on the reservoir volume maintaining its evacuated or compacted state after being mechanically operated upon. Folding the reservoir is not the preferred method of reservoir evacuation and is only shown for completeness of disclosure.

Figure 4B:
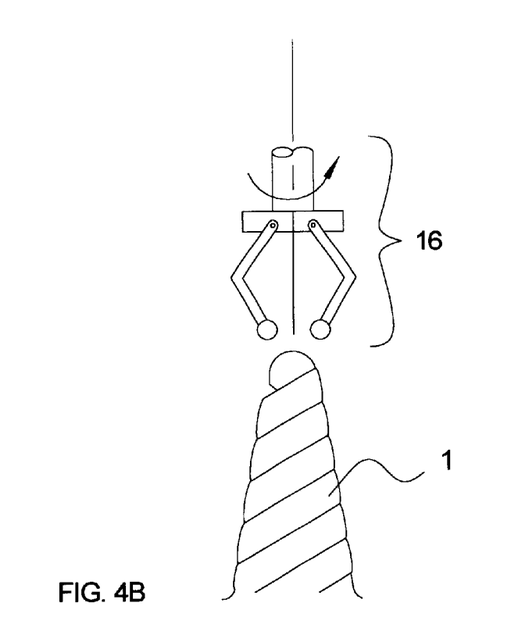
FIG. 4B shows a mechanical twisting mechanism to be used for twisting a reservoir volume of a glans sheath.

FIG. 4B shows a reservoir winding tool 16 and a successfully wound reservoir 1. The tool grips the reservoir near the tip of the reservoir and simply performs revolutions to wind the reservoir about itself until satisfactory air evacuation has been achieved. Axial plunge capability of the winding tool can be made to compensate for any reservoir height changes as the reservoir is being wound. Winding of the reservoir is the preferred reservoir packaging technique.

Figure 4C:
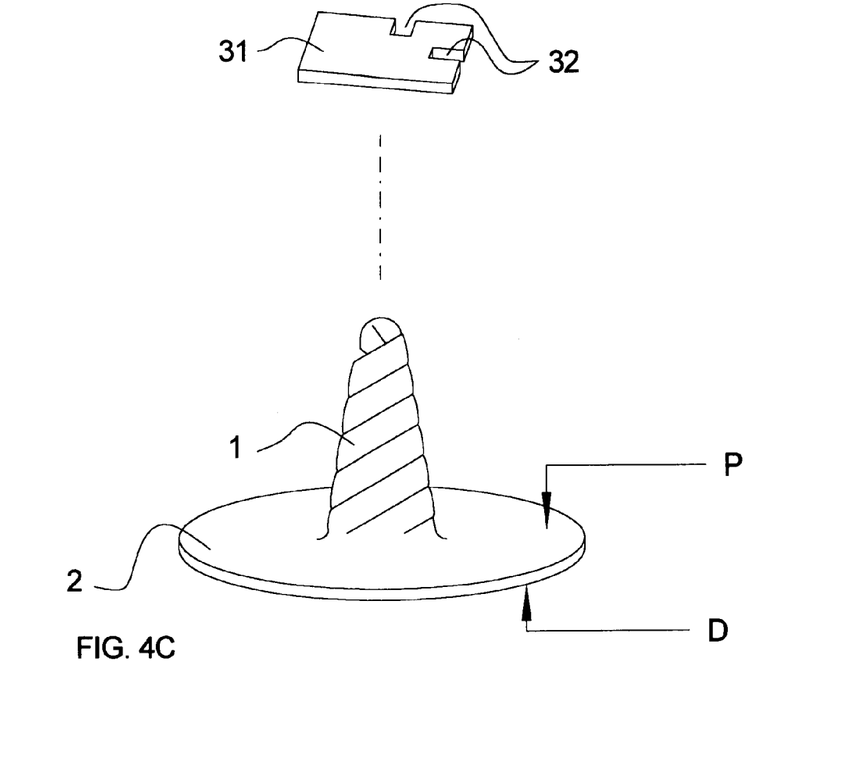
FIG. 4C shows a twisted reservoir volume of a glans sheath and a mechanical clip which can secure the reservoir volume.
Figure 4D:
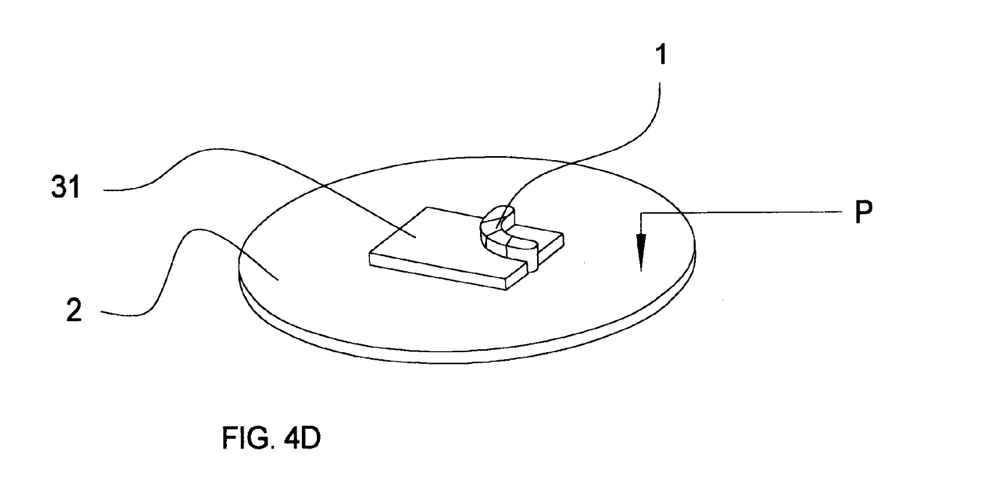
FIG. 4D shows a mechanical clip securing a twisted reservoir volume.

FIG. 4C shows a mechanical clip 31 that has a plurality of notches 32 cut out from the clip. The clip is preferably made from an elastomeric material such as latex but can be made from hundreds of pliable materials known in the art. The notches are cut so as to allow the twisted reservoir to slip into them to remain wound during coitus yet slip free from the notches during deployment as the reservoir fills with ejaculate. FIG. 4D demonstrates the clip 31 securing a twisted reservoir volume 1 by looping the twisted reservoir volume through the plurality of notches 32 so as enable the material of the wound reservoir to lie adjacent to the flange of the device. The twisted reservoir volume 1 is wrapped about the notches 32 of the mechanical clip so as to prevent the twisted volume from unwinding until pressure from seminal fluid enters the reservoir volume. When the reservoir deploys, the reservoir will be pulled distally from the notches, and the reservoir volume will fill and untwist itself.

Figure 5A:
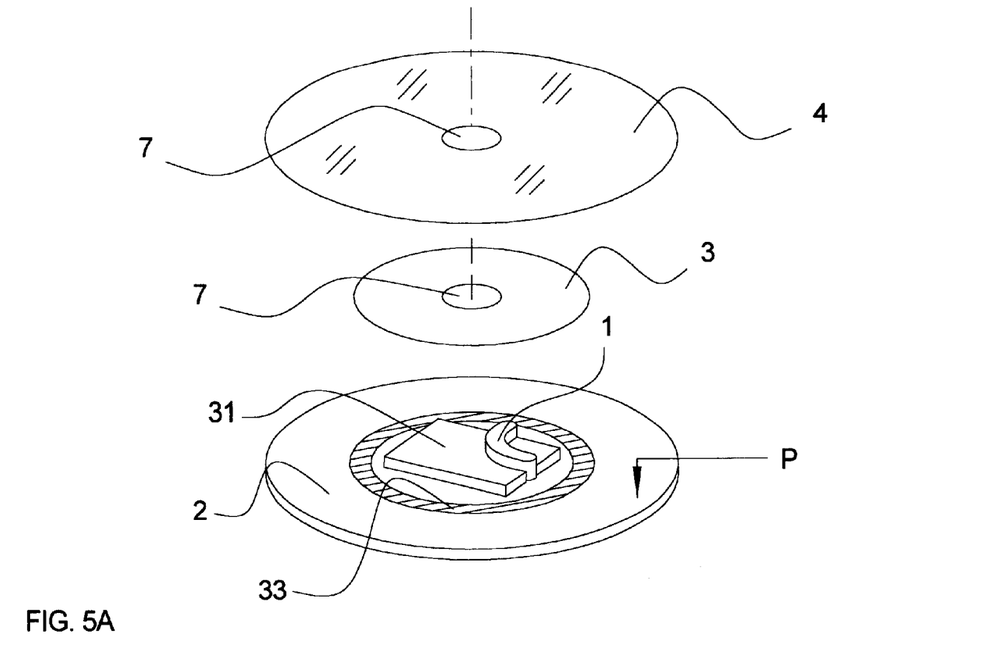

A minimal percentage of the proximal surface of the flange will need to be covered with medically approved adhesive to adhere the flange to the glans penis of the user. Various different medical adhesive films are available in the art that suit the design such as 3M 1509 double sided transfer film. FIG. 5A illustrates a disk of medically approved, double sided adhesive film 4 being applied to the proximal surface of an annular-like flange 2 after the previous operations have been completed. The adhesive disk 4 is of the same general shape as the annular-like flange and has a through-hole 7 to allow the passage of ejaculate into the reservoir. Preferably the adhesive film 4 is large enough to cover the entire surface of the flange 2 except for that area of the through hole 7. The through-hole also passes through a disk of plastic film 3 which is adhered to the surface of the adhesive film 4 and approximately coaxial to the adhesive disk. The disk of plastic film 3 prevents the double sided adhesive film from adhering to the compacted reservoir 1. The reservoir needs to be able to deploy to perform its function and would be unable to do so if held fast by the adhesive film 4. The disk of plastic film also forms the floor of the reservoir volume when filled with ejaculate. As a design alternative, the disk of plastic film could be welded to the flange material over the compacted reservoir 1 and clip 31. The disk of plastic film could be welded using a technique known in the art such as ultrasound welding and could be welded down in a weld pattern 33 shown by the cross-hatched area in the figure. A weld pattern creates a localized stress area in the flange and is not the preferred manufacturing technique. It is disclosed for completeness.

Figure 5B:
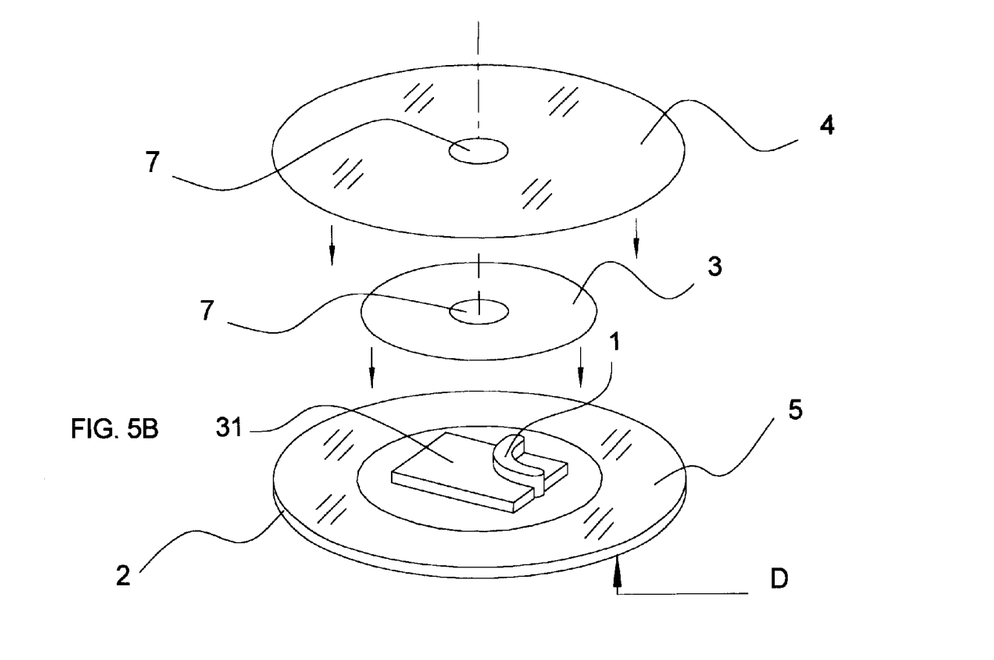

FIG. 5B shows an alternative layout for putting medically approved, double sided adhesive fim on the proximal surface of the flange. In the figure, a first toroid of medically approved, double sided adhesive film 5 in the general shape of the annular-like flange is applied to the proximal surface of the flange 2 such that it is approximately coaxial to the flange. Multiple layers of toroids could be applied to the flange but a single layer of double sided adhesive film is adequate. A disk of plastic film 3 is adhered to the toroid. The disk of plastic film 3 also has a through-hole 7 to allow the passage of ejaculate into the reservoir. The disk of plastic film 3 has an outer diameter slightly larger than the inner diameter of the toroid of film 5 bonded to the flange. The disk is adhered in a manner which secures the perimeter of the disk to the toroid such that the perimeter of the disk overlaps the inner diameter of the toroid. The intent of the toroid shaped film is to secure the perimeter of the disk of plastic film 3 so as to prevent the intiation of crevasses or fissures radially outward along the floor of the reservoir volume as the reservoir pressurizes from ejaculate. These crevasses or fissures could mature into leakage channels for pressurized seminal fluid. The adhesive film 4 is applied lastly over the toroid shaped adhesive film 5 bonded to the flange and the disk of plastic film. The adhesive disk 4 has a through-hole 7 to allow the passage of ejaculate into the reservoir. The adhesive disk 4 is of the same general shape as the annular-like flange and preferrably covers the entire surface of the flange 2 except for that area of the through hole 7. A suitable medical film for both the toroid shape 5 and the disk shape 4 is 3M #1509 medical transfer film. The preferred design has a material stack including a first toroid of double sided medical film 5 bonded to the proximal surface of the flange, a disk of plastic film 3 overlapping the inner diameter of the toroid and secured to the toroid about the disk perimeter and also forming the floor of the reservoir and finally, a disk of double sided adhesive film 4 covering over the toroid of film and the disk of plastic film.

Figure 6A:
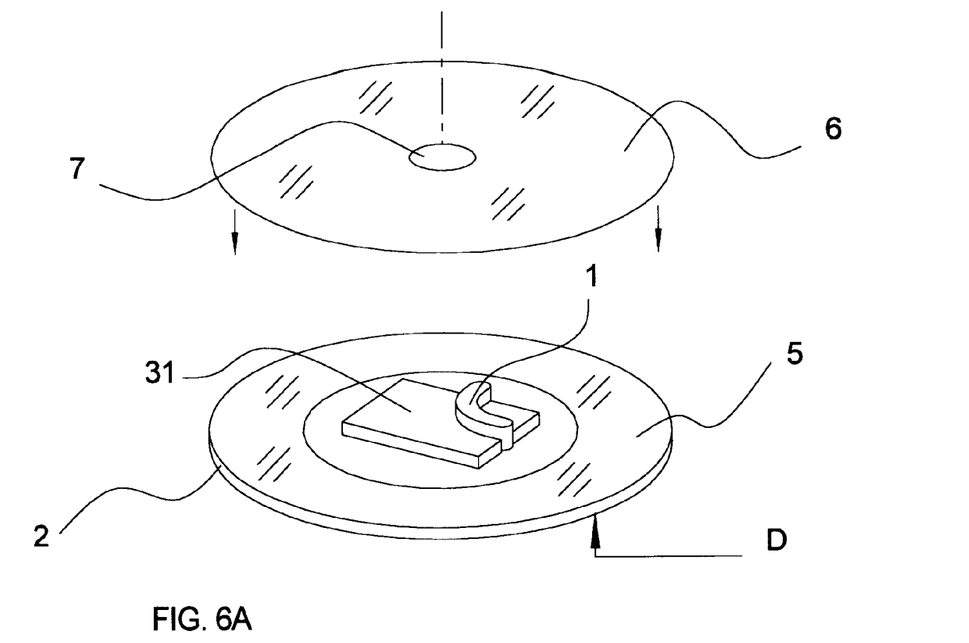

FIG. 6A shows another alternative method of covering the annular-like flange 2 with adhesive film. In this method a toroid of medically approved, double sided adhesive film 5 in the general shape of the annular-like flange is applied to the proximal surface of the flange 2 to be approximately coaxial to the flange. Multiple layers of toroids could be applied to the flange if desired for design intent. A disk of single-sided, medically approved adhesive film 6, such as any of several of 3M single-sided medical adhesive films, has the same general shape as the annular-like flange and is adhered to the toroid such that the adhesive on the film 6 remains proximally exposed and the backing of the single sided film covers over the compacted reservoir 1. The backing of the single sided adhesive protects the compacted reservoir from any adhesive used to bond the flange to a glans penis thereby allowing the reservoir to deploy when needed. A through-hole 7 is approximately centered in the disk of single sided adhesive film 6 to permit the unimpeded passage of ejaculate into the reservoir.

Figure 6B:
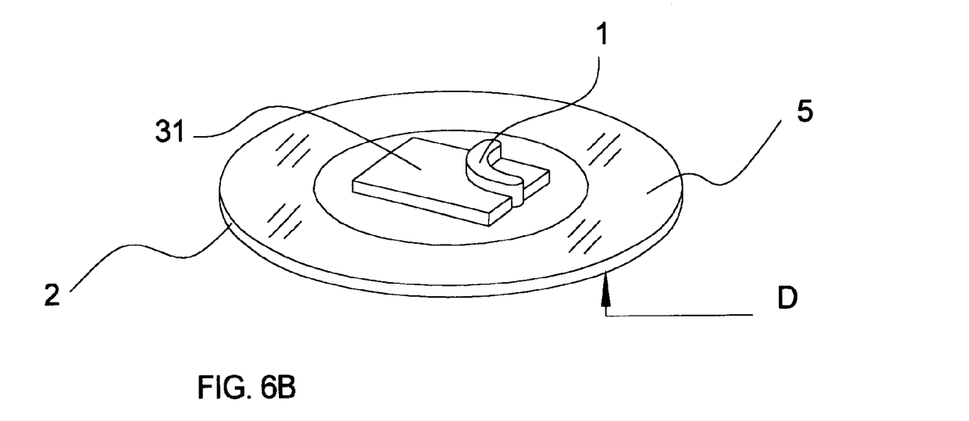

FIG. 6B shows a minimal material design wherein a toroid of medically approved, double sided film 5 in the same general shape as the annular-like flange 2 lies over the proximal surface of the flange. Multiple layers of the toroid shaped film could be stacked onto the proximal surface but one layer will suffice. Minimally the adhesive film could extend inwardly from the perimeter of the flange to cover only 40% of the proximal surface of the flange and still present acceptable bonding capability. This design does nothing to protect the compacted reservoir 1 and greatly reduces usable bonding area of the adhesive. This design is not preferred and is disclosed only for completeness.

Figure 7A:
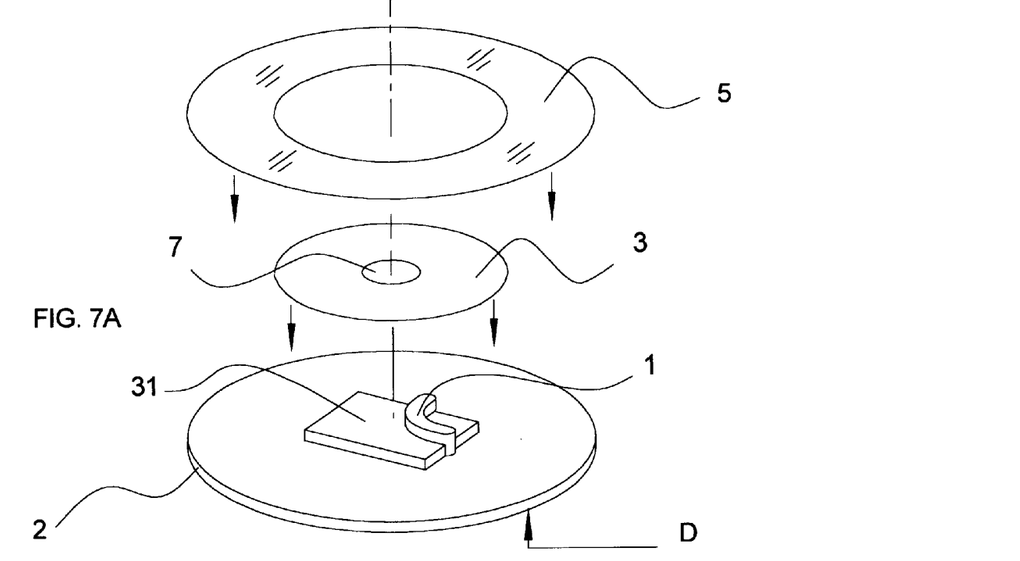
Figure 7B:
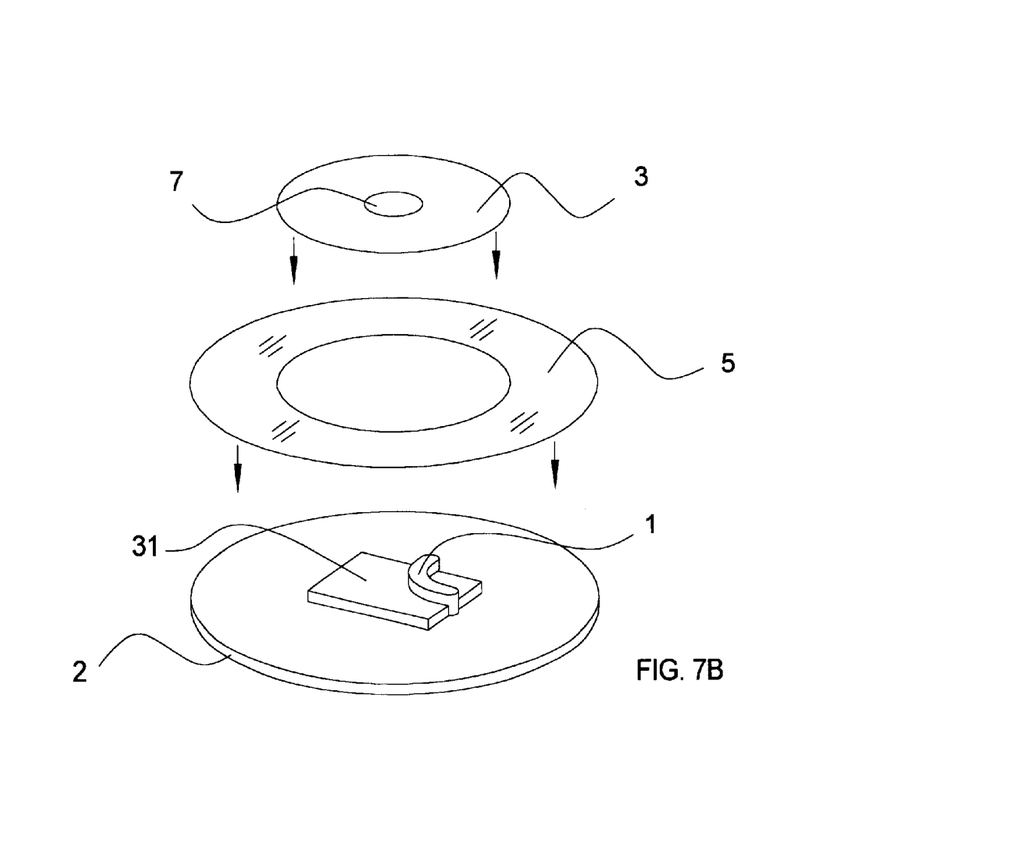

Other designs using minimal bonding surface area are shown in FIGS. 7A and 7B. In these designs a disk of plastic film 3 is used to cover over the compacted reservoir 1 to protect the reservoir. The disk of plastic film and the toroid of double sided film 5 are approximately coaxial to the annular-like flange 2. The disk of plastic film has a through-hole 7 to permit the unimpeded flow of ejaculate into the reservoir. In all designs the disk of plastic film could be manufactured from polyethylene film such as the stretch film preferrably used to manufacture the glans sheath device but many other suitable plastic films are available for use. In FIG. 7A the disk of plastic film 3 is first applied to the proximal surface of the annular like flange and the toroid of adhesive film 5 is adhered over the plastic disk to secure the disk 3 to the annular-like flange 2. In FIG. 7B the toroid of adhesive film 5 is adhered to the annular-like flange and the disk of plastic film 3 is adhered to the toroid. A second toroid shape could be placed over the disk of plastic film to sandwich the disk between layers of adhesive. Multiple layers of toroid shaped adhesive layers could be stacked upon each other as well with the disk of plastic film located somewhere in the stack to form the floor of the reservoir volume. These designs are also not preferred and are only disclosed for completeness.

Figure 8:
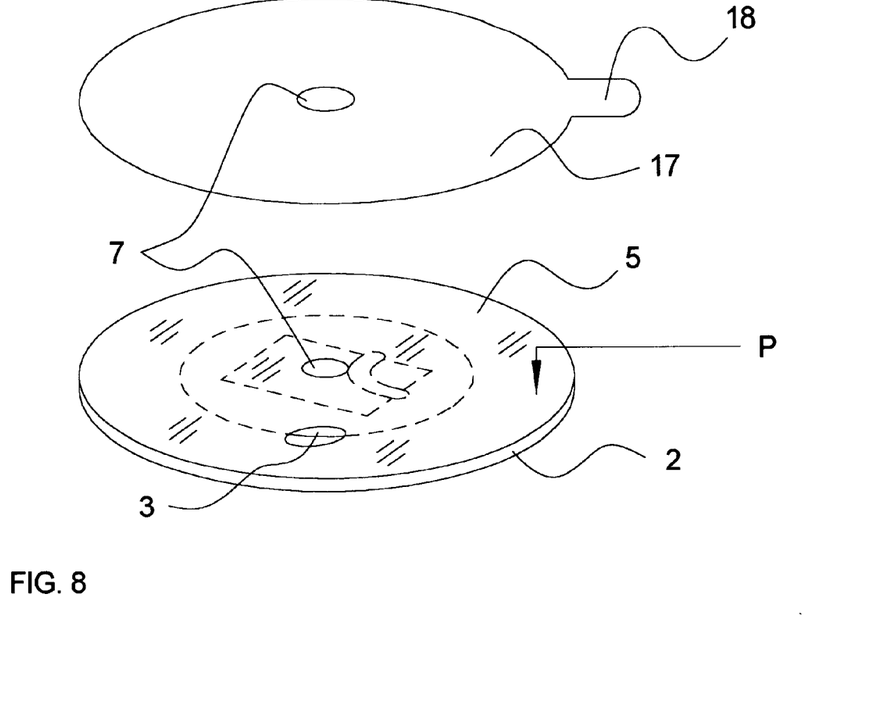
FIG. 8 shows a protective member with a tab being applied to the adhesive film on the proximal surface of the annular flange of a glans sheath.

FIG. 8 shows a protective member 17 with an optional tab 18 wherein the protective member covers over the proximal surface of an adhesive film to protect the adhesive until the glans sheath is bonded to a glans penis via the annular-like flange 2. A cutaway of the adhesive film has been made to show the disk of plastic film 3 positioned between the compacted reservoir and the adhesive film. Preferrably the protective member, the adhesive film adhered to the flange and a disk of plastic film, if used, would all be installed at the same time to simplify assembly. For handling purposes the adhesive film is usually already placed on a protective backing as a manufacturing step. Centering a disk of plastic film 3 on a cutout of adhesive film adhered to a protective backing is an easy manufacturing task. Punching a hole through all plastic disk, adhesive and protective materials is easy as well. The combination of a protective backing, adhesive film, plastic disk as an assembly is easily centered to cover over the proximal surface of the annular-like flange to achieve the design intent of creating a glans sheath mininmally having a reservoir and an annular-like flange with an adhesive film covering the proximal surface of the flange.

Figure 9:
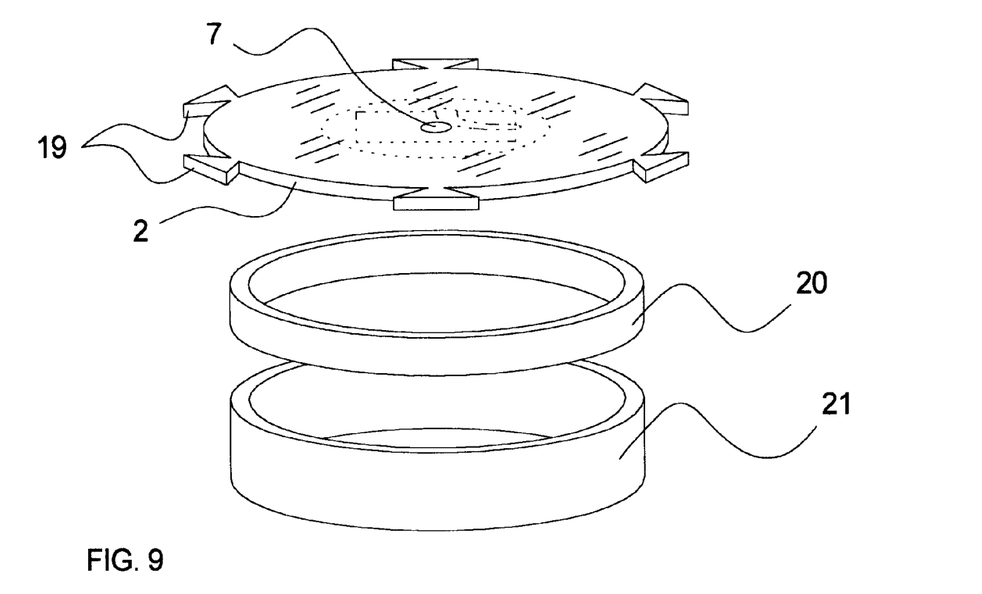
FIG. 9 shows a rigid multi-piece mechanism for tautly restraining the annular flange of a glans sheath which has been manufactured by the disclosed methods.

The glans sheath device is intended to be manufactured from a very pliable material so as to conform to the natural shape of the glans penis and also to avoid causing discomfort to either partner during coitus. Handling a very pliable flange becomes an issue. To prevent fissures and crevasses between the annular-like flange and the surface of the glans penis, it is important to be able to press the flange surface flatly against the skin of the glans during adhesion. This is critically important to the function of the sheath and is an unmanageable task if done by manually gripping the flange with fingers to apply the flange to the glans penis. A method of handling the pliable flange is necessary for proper application. FIG. 9 shows a concept for a method to handle the pliable flange during the flange to glans bonding process. Around the perimeter of the annular-like flange 2 are a multiplicity of restraining legs 19 approximately evenly spaced about the perimeter. The thinnest cross-section of the leg is where the leg is attached to the flange either integrally or by adhesive means. Under tensile load in excess of yield strength of the leg material, the thinnest cross-section is where the leg would fail by design. By tensioning these legs against each other below the leg yield strength, the flange is stretched taut. By stretching the flange over a rigid restraining tool composed of at least two parts, part A 20 and part B 21, and securing the legs 19, the flange can be held in a taut condition during the process of bonding the flange to the glans penis. The user can grasp the rigid tool and easily position the flange such that the through-hole 7 is positioned closely to the urethral opening in the penis without creasing or folding the flange over itself. This overcomes a major design flaw of previous designs which required manual handling of the flange. As will be discussed shortly, the restraining legs of the instant invention are only intended as a flange tensioning means during the flange bonding process and are separated from the flange immediately after successful flange bonding.

Figure 10A:
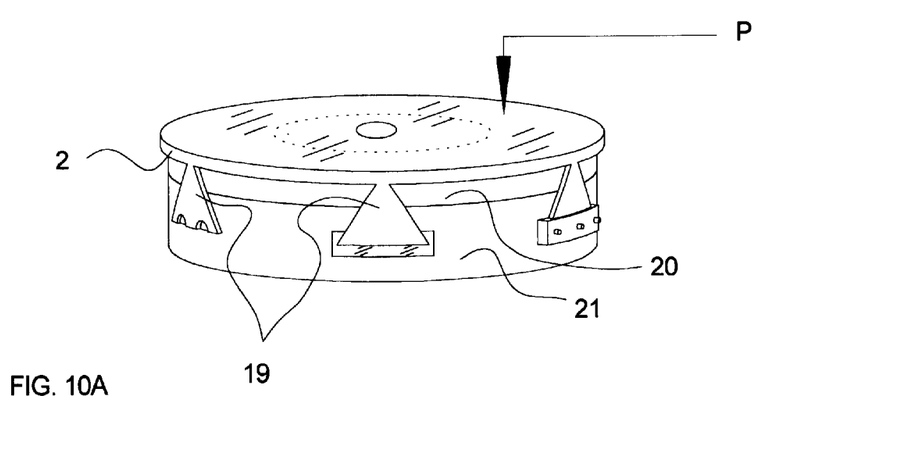
FIG. 10A shows a protective member with a tab being applied to the adhesive film on the proximal surface of the annular flange of a glans sheath which has been tautly restrained over a rigid multi-piece mechanism by a variety of restraining methods.

FIG. 10A illustrates how the legs 19 about the perimeter of the annular-like flange 2 can be secured to part B 21 of the restraining tool with part A 20 being held between restraining tool part B and the distal surface of the flange. The legs are simultaneously stretched over part A to bring the flange into a taut state and then they are fastened to part B while maintaining the taut state of the flange. The two piece design allows the user to nearly axially separate the two pieces, part A and part B, away from each other simply by applying approximately axially oriented forces to the two pieces. This design feature is leveraged during the glans bonding process.

Figure 10B:
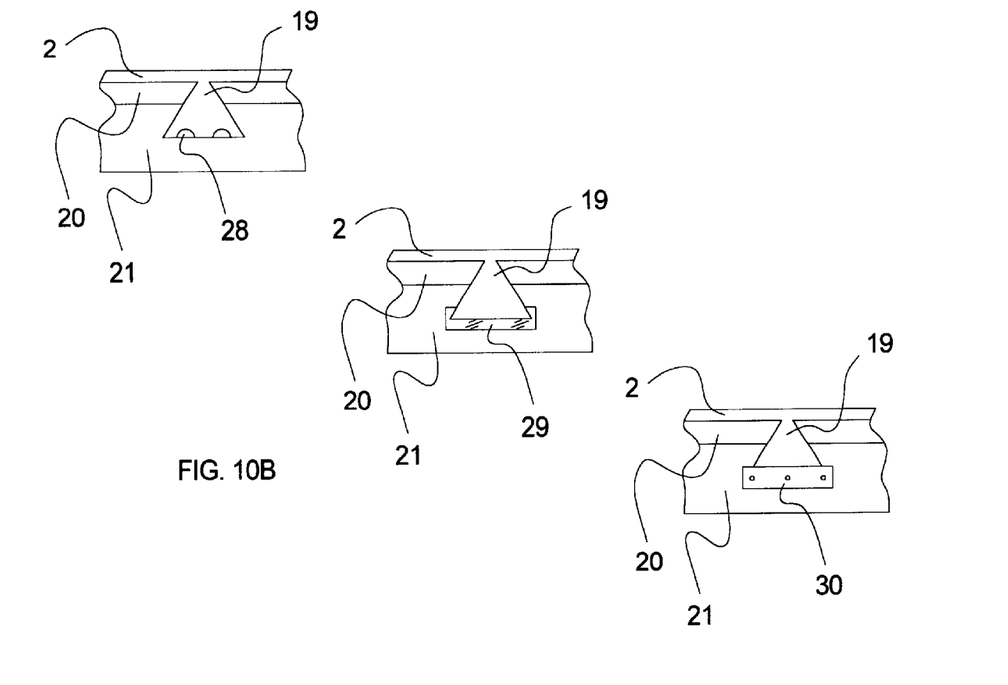
FIG. 10B shows a variety of methods to secure a leg of a glans sheath annular flange onto a multi piece, taut-restraint mechanism.

FIG. 10B illustrates several different methods to secure the restraining legs 19 against the restraining tool part B 21. A welding technique 28, such as ultrasonic spot welding, an adhesion technique 29, such as double sided tape, or a mechanical clamping technique 30 such as interference fit of multiple ring inner and outer diameters can be used for securing purposes. These and several other securing methods are available and need only serve to secure the restraining legs to maintain the flange 2 in a taut state during the flange to glans bonding process.

Figure 11A:
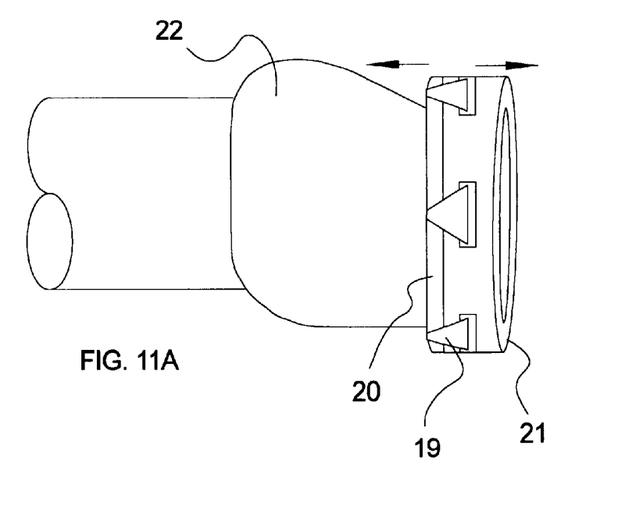
FIG. 11A shows a glans sheath manufactured by the disclosed methods and tautly restrained by a multi-piece, taut-restraint mechanism being bonded onto a glans penis and also illustrates the separating action of the multi-piece mechanism.

The flange to glans penis bonding process is shown in FIG. 11A. A protective member has been removed to uncover the adhesive on the proximal surface of the flange and is not shown. The restraining legs 19 hold the flange taut during the bonding process as the flange is pressed against the skin of the glans penis 22. During the bonding operation the user grasps part A 20 and presses it against the glans penis to adhere the proximal surface of the flange onto the glans. While pressing part A against the glans, the user simultaneously pulls on part B 21. The thinnest cross-section of the restraining legs 19 fails under the tensile load induced by the user pulling the two tool pieces apart, and the legs tear away from the perimeter of the flange. The arrows in the figure illustrate the direction of the nearly axial forces acting on parts A and B.

Figure 11B:
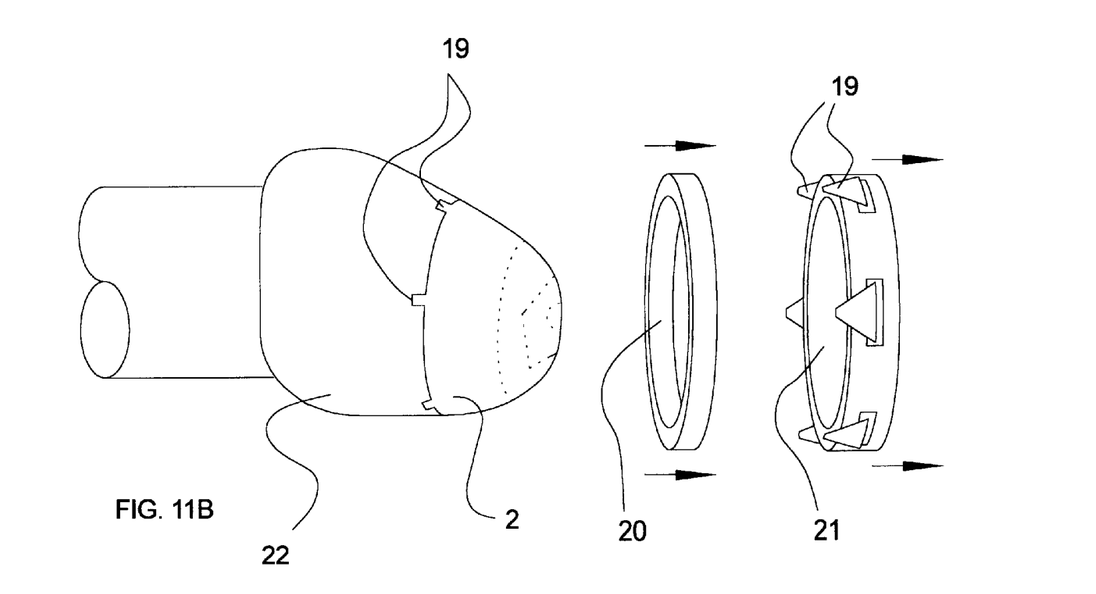
FIG. 11B shows a glans sheath bonded onto the glans penis of a user and the removal of the individual parts which had been tautly stretching the annular flange of the glans sheath prior to flange bonding.

FIG. 11B illustrates the restraining tool parts A 20 and B 21 being removed from the glans after a successful flange to glans bonding operation. Arrows in the figure show the removal direction of the restraining tool parts. The restraining legs 19 remain secured to part B. The flange 2 has been bonded onto the glans penis 22 without crevasses or fissures and has thereby created a seal about the urethra. The glans sheath has been positioned such that the compacted reservoir volume is proximally oriented and is in place near the urethral opening to capture and contain ejaculate.

Figure 12A:
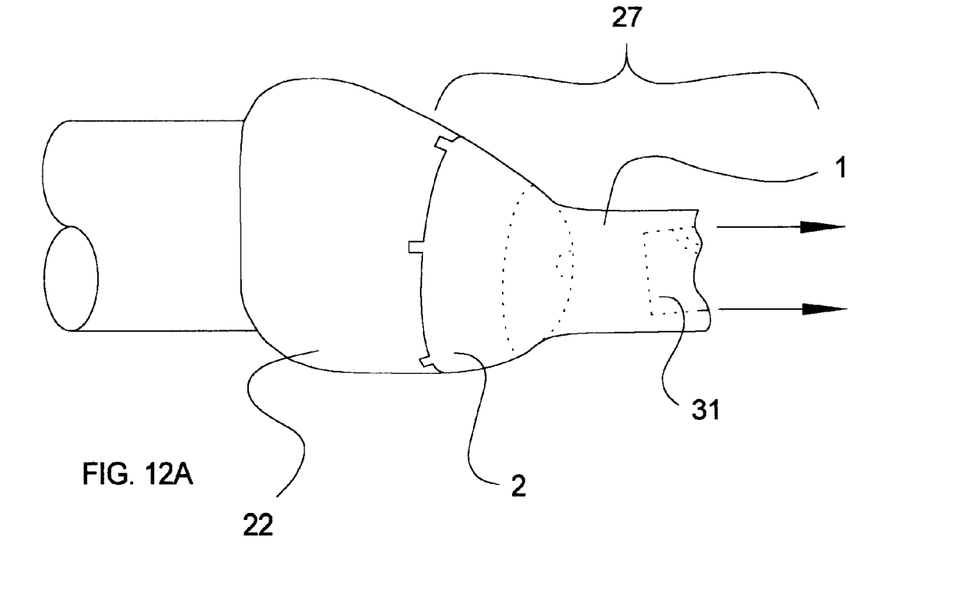
FIG. 12A shows the evacuated, folded reservoir of a glans sheath in mid-deployment as the reservoir volume fills with ejaculate.

FIG. 12A illustrates the reservoir volume 1 deploying as ejaculate would begin filling the reservoir. The reservoir material deploys outwardly in the distal direction with the tip of the reservoir as the last part of the reservoir to deploy. Arrows in the figure show the direction of the reservoir deployment.

Figure 12B:
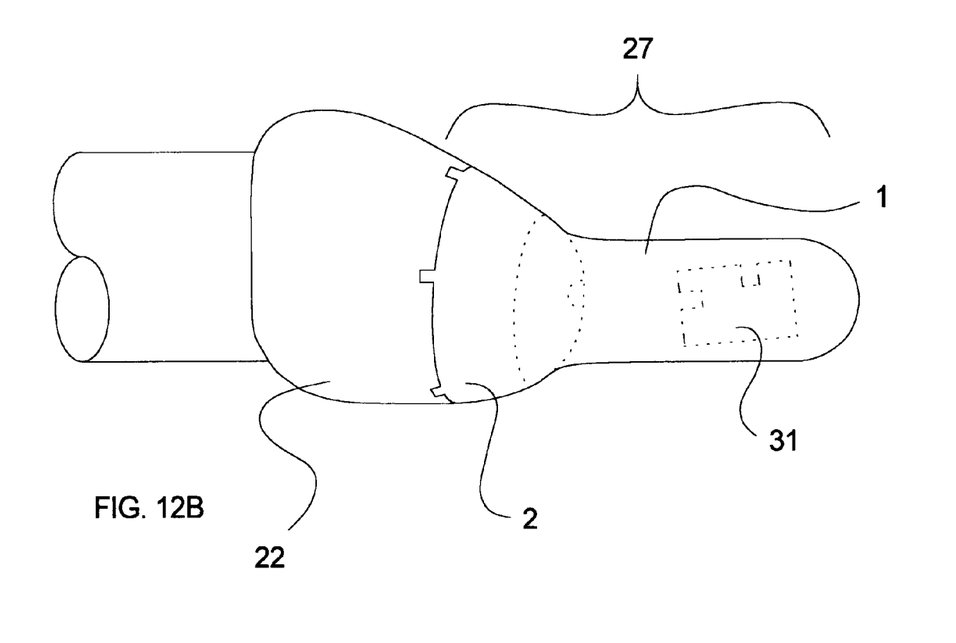
FIG. 12B shows a fully deployed reservoir volume of a glans sheath after the reservoir volume has been filled with ejaculate.

FIG. 12B illustrates the reservoir 1 of the glans sheath 27 being fully deployed caused by the delivery of ejaculate into the reservoir. The glans sheath can later be removed and discarded in a proper manner. The reservoir of the glans sheath is able to contain between 3 and 14 cc's but preferably contains 8 cc's of fluid and has a mean diameter between 0.375 and 1.25 inch but preferably has a mean diameter of 0.75 inch and has a spherical tip of radius equal to one half the mean diameter. The annular-like flange 2 of the glans sheath has an outer diameter between 1.0 and 2.5 inches but preferably is 1.75 inches. Preferably a disk of plastic film 1.0 inch in diameter covers over the compacted reservoir to separate the reservoir from a film of double-sided, medically-approved adhesive covering the proximal surface of the flange. The mean thickness of the glans sheath material could be from 0.4 mils to 5 mils in thickness but preferably is 0.8 mils. Preferably a protective backing over the adhesive on the flange has a diameter equivalent to the diameter of the adhesive but may be oversized for ease of gripping. Preferably the protective backing has a tab measuring 0.25 inches by 0.25 inches.

By manufacturing a glans sheath device according to this method, a user has a device which contains a reservoir volume large enough to contain approximately 8 cc's of seminal discharge yet protects the large reservoir volume from damage until it is flooded and deployed according to the design. The device is easily handled for successful adhesion to the glans penis by means of a multiple part restraining tool. Providing such a device to the public will help to improve family planning strategies and also help to reduce the passage of sexually transmitted diseases spread by the intermixing of seminal and vaginal fluids.

While the embodiments described herein are at present considered to be preferred, it is understood that various modifications and improvements may be made therein without departing from the invention. The scope of the invention is indicated in the appended claims and all changes that come within the meaning and range of equivalency of the claims intended to be embraced therein.

I claim:

1. A prophylactic device adapted to be worn on a user's glans penis, comprising:
   a) an annular flange;
   b) a means contained on a proximal side of said annular flange for attaching the flange to a user's glans penis; and
   c) a reservoir attached to the annular flange for receiving ejaculate from the user, wherein the reservoir is collapsed and folded on said proximal side of the annular flange such that the reservoir is substantially free of air volume.

2. The device of claim 1, wherein said reservoir is integrally formed with said flange as a structure of unitary construction.

3. The device of claim 2, wherein said reservoir is flexible, collapsible and expandable.

4. The device of claim 1, wherein the annular flange further includes a plurality of radial legs extending outwardly from and beyond said annular flange.

5. The device of claim 4, wherein said plurality of radial legs and said annular flange are an integral structure of unitary construction.

6. The device of claim 4, wherein said reservoir, said annular flange, and said plurality of radial legs are an integral unit of unitary construction.

7. The device of claim 4, further comprising a semi-rigid support structure affixed to each of said radial legs.

8. The device of claim 7, wherein said semi-rigid support structure includes a first member having a through-passage and in connection with a second member suitable for attachment to each of said radial legs.

9. The device of claim 8, wherein said semi-rigid support structure comprises at least two ring members, wherein said radial legs of the annular flange are attached to a distal-most ring member such that the flange is stretched taut.

10. The device of claim 1, wherein said attachment means includes an adhesive layer adhesively applied to said annular flange.

11. The device of claim 10, further comprising a removable protective member covering said adhesive layer over the annular flange.

12. The device of claim 11, further comprising a tab integrally connected to the removable protective member to facilitate removal thereof from the annular flange prior to use of the device.

13. The device of claim 1, wherein said reservoir is twisted until substantially devoid of air volume.

14. The device of claim 13, further including means for retaining the twisted reservoir adjacent to said proximal side of the annular flange.

15. A method of manufacturing a prophylactic device for a glans penis, wherein the device includes a reservoir for seminal fluid attached to an annular flange, the method comprising the steps of:

a) shaping the reservoir in a plastic film;

b) collapsing the reservoir of step a on a proximal side of said annular flange, such that the reservoir is substantially devoid of air volume;

c) folding the reservoir of step b at least once on said proximal side of the annular flange; and d) applying an adhesive to the proximal side of the annular flange while leaving said reservoir free of said adhesive.

16. The method of claim 15, wherein an exterior sidewall of said reservoir further includes a low-tack adhesive.

17. The method of claim 16, wherein said low-tack adhesive comprises double-sided tape.

18. The method of claim 16, wherein only a portion of said exterior sidewall contains said low-tack adhesive such that only sidewall-to-sidewall bonding is achieved.

19. The method of claim 15, wherein step b is carried out by twisting the reservoir until said reservoir is substantially devoid of air volume.

20. The method of claim 19, wherein step c is carried out by looping the reservoir about a retaining means and retaining the reservoir adjacent to said proximal side of the annular flange.

21. The method of claim 15, wherein step c is carried out by folding the reservoir substantially flush with said annular flange.

* * * * *